(12) United States Patent
Pan et al.

(10) Patent No.: US 8,637,444 B2
(45) Date of Patent: Jan. 28, 2014

(54) COMPOSITIONS AND METHOD OF DELIVERY

(75) Inventors: Long Pan, Cherry Hill, NJ (US); Claudio Ortiz, Dayton, NJ (US); Allen Puchalski, Lawrenceville, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/505,859

(22) PCT Filed: Nov. 5, 2010

(86) PCT No.: PCT/US2010/055648
§ 371 (c)(1),
(2), (4) Date: May 3, 2012

(87) PCT Pub. No.: WO2011/057090
PCT Pub. Date: May 12, 2011

(65) Prior Publication Data
US 2012/0225806 A1 Sep. 6, 2012

Related U.S. Application Data

(60) Provisional application No. 61/258,650, filed on Nov. 6, 2009.

(51) Int. Cl.
*A61L 101/02* (2006.01)

(52) U.S. Cl.
USPC .......................................................... 512/4

(58) Field of Classification Search
USPC .......................................................... 512/4
See application file for complete search history.

(56) References Cited

U.S. PATENT DOCUMENTS

2004/0258903 A1* 12/2004 Eberle ........................ 428/317.9
2008/0206093 A1   8/2008 Muller et al.

FOREIGN PATENT DOCUMENTS

| WO | WO 2004045759 A2 * | 6/2004 |
| WO | WO 2006/125739 | 11/2006 |
| WO | WO 2007/035596 | 3/2007 |
| WO | WO 2007035596 A2 * | 3/2007 |
| WO | WO 2009/133278 | 11/2009 |

OTHER PUBLICATIONS

Lan, et al. (Inorg. Chem. 2009, 48, 7165-7173, "RMP3: A Multifunctional Microporous MOF with Recyclable Framework and High H2 Binding Energy").*

Dinca, et al. (Journal of American Chemical Society, 2005, 127, 9376 "Strong H2 Binding and Selective Gas Adsorption within the Microporous Coordination Solid Mg3(O2C-C10-H6-CO2)3").*

BASF, 2008, hand out, 051908, "BASOLITE Metal Organic Frameworks".

Dinca et al, 2005, "Strong $H_2$ Binding and Selective Gas Adsorption within the Microporous Coordination Solid $Mg_3(O_2C-C_{10}H_0-CO_2)_3$", J.Am.Chem. Soc., 127(26):9376-9377.

Horcajada et al, 2006, "Metal-Organic Frameworks as Efficient Materials for Drug Delivery", Angew Chem., 45:5974-5978.

Horcajada et al, 2008, "Flexible Porous Metal-Organic Frameworks for a Controlled Drug Delivery", J.Am Chem. Soc., 130:6774-6780.

Lan et al, 2009, "RPM3: A Multifunctional Microporous MOF with Recyclable Framework and High $H_2$ Binding Energy", Inorg. Chem. 48:7165-7173.

Lan et al, 2009, "A Luminescent Microporous Metal-Organic Framework for the Fast and Reversible Detection of High Explosives", Angew Chem., 48:2334-2338.

Ni et al, 2006, "Rapid Production of Metal-Organic Frameworks via Microwave-Assisted Solvothermal Synthesis", J. Am. Chem. Soc. 128:12349-12395.

Pan et al, 2000, "Novel Single- and Double-Layer and Three-Dimensional Structures of Rare-Earth Metal Coordination Polymers: The Effect of Lanthamide Contraction and Acidity Control in Crystal Structure Formation", Angew Chem., 39:527-530.

Pan et al, 2003, "RPM-2: A Recyclable porous material with unusual adsorption capability: self assembly via structural transformation", Chem. Commun., pp. 854-855.

Pan et al, 2003, "Porous Lanthanide-Organic Frameworks: Synthesis, Characterization, and Unprecedented Gas Adsorption Properties", J. Am Chem Soc., 125:3062-3067.

Pan et al, 2003, "RPM-1: A Recyclable Nanoporous Material Suitable for Ship-In-Bottle Synthesis and Large Hydrocarbon Sorption", Angew Chem., 42:542-546.

Pan et al, 2004, "Microporous Metal Organic Materials: Promising Candidates as Sorbents for Hydrogen Storage", J. Am Chem Soc., 126:1308-1309.

Pan et al, 2006, "Separation of Hydrocarbons with a Microporous Metal-Organic Framework", Angew Chem., 45:616-619.

(Continued)

*Primary Examiner* — Ling Choi
*Assistant Examiner* — Lanee Reuther
(74) *Attorney, Agent, or Firm* — Michael F. Morgan

(57) ABSTRACT

A method of delivering a material to a person comprising applying an anhydrous composition to a person, wherein the anhydrous composition comprises a base and metal organic framework formed from a recyclable porous material with the material adsorbed into the metal organic framework, and the recyclable porous material has a structure that breaks down when contacted with water to release the material. An anhydrous composition comprising a base and a metal organic framework formed from a recyclable porous material with the material adsorbed into the metal organic framework, wherein the recyclable porous material has a structure that breaks down when contacted with water to release the material.

9 Claims, No Drawings

(56) References Cited

OTHER PUBLICATIONS

Pan et al, 2006, "Zn(tbip) (H2tbip=5-tert-Buty) Isophtalic Acidy a Highly Stable Guest-Free Microporous Metal Organic Framework with Unique Gas Separation Capability", J. Am Chem Soc., 128:4180-4181.

SIGMA-ALDRICH, 2009, www.sigmaaldrich.com/catalog/search/ProductDetail/ALDRICH/688738, (Basolite™ A 100), downloaded Oct. 27, 2009.

Wikipedia, 2009, "Metal-Organic Framework".

International Search Report and Written Opinion for International Application No. PCT/US2010/055648 mailed on Jul. 19, 2012.

* cited by examiner

COMPOSITIONS AND METHOD OF DELIVERY

CROSS REFERENCE TO RELATED APPLICATIONS

This application is a national stage entry under 35 U.S.C. §371 of International Patent Application No. PCT/US2010/055648, filed 5 Nov. 2010, which claims priority to U.S. Provisional Patent Application No. 61/258,650, filed on 6 Nov. 2010, which is incorporated herein by reference.

BACKGROUND

There are many ways to deliver a material to a person. For some materials, the delivery may be more difficult because the material may volatilize away once delivered to a person, or the material may adversely interact with other ingredients in a composition to reduce the level of the material. Also, it would be desirable to deliver a material to a person and have the material available when needed.

For personal care products, fragrance is used to provide a pleasant aroma to the product and the person. Fragrance longevity is desired to continue delivering the fragrance after the product has been applied. While fragrances can be encapsulated in various materials, there usually needs to be some mechanical action that breaks down the encapsulate to release the material. When the personal care product is an antiperspirant/deodorant, it would be desirable to release fragrance when needed during sweating.

SUMMARY

A method of delivering a material to a person comprising applying an anhydrous composition to a person, wherein
a) the anhydrous composition comprises a base and metal organic framework formed from a recyclable porous material (RPM) with the material adsorbed into the metal organic framework, and
b) the recyclable porous material has a structure that breaks down when contacted with water to release the material.

An anhydrous composition comprising a base and a metal organic framework formed from a recyclable porous material (RPM) with the material adsorbed into the metal organic framework, wherein the recyclable porous material has a structure that breaks down when contacted with water to release the material.

DETAILED DESCRIPTION

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

A metal organic framework (MOF) can be used to adsorb material into the pores in its structure. As used herein, the MOF does not include all MOF structures. The MOF is a recyclable, porous material (RPM), which is capable of breaking down when contacted with water. By selecting an RPM, the material can be released when contacted with water. RPMs are known. By breaking down, the bonds in the RPM that form the framework are broken, which collapses the framework structure. When the structure if broken, the material is released.

In MOFs that have been used previously to hold fragrances, the MOFs have been based on structures similar to zeolite. In these structures, the structures are more stable in water, and they maintain their structure. They release fragrances or other materials by displacement of some of the material when contacted with water. The MOF materials are kept in an anhydrous condition until use. When contacted with water, water flows into the MOF structure to displace the material. An equilibrium is reached between the material and water in the bulk composition and the material and water in the MOF structure. The equilibrium can continue to change if the material, such as a fragrance, is volatile and leaves the bulk composition. At this time, more material will move from the MOF to the bulk composition. With these types of MOF structures, it takes time to release the material, and depending on the conditions, not all of the material will be released from the MOF structure. It would be desirable to release all of the material to the bulk composition to avoid waste of the material.

The RPMs described herein are capable of having their structure broken down so that up to 100% of the material can be released.

In certain embodiments, the RPM contains a metal node that is connected with ligands. For use with compositions that will come into contact with people, the metal can be selected from Mg, Ca, Al, Zn, Fe, and Co. In certain embodiments, the ligands can be selected to be amino acids or food additives, such as citric acid.

One RPM that can be used is $[Co_3(biphenyldicarboxylate)_3 4,4'$-bipyridine$].4DMF.H_2O$. Information can be found in RPM-1: A Recyclable Nanoporous Material Suitable for Ship-In-Bottle Synthesis and Large Hydrocarbon Sorption, Long Pan et al., Angew. Chem. Int. Ed. 2003, 42, No. 5, pp. 542-546, which incorporated herein by reference in its entirety. In this publication, $[Co_3(biphenyldicarboxylate)_3 4,4'$-bipyridine$].4DMF.H_2O$ is referred to as $[Co_3(bpdc)_3bpy].4DMF.H_2O$, wherein bpdc is biphenyldicarboxylate and bpy is 4,4'-bipyridine, and DMF refers to N,N-dimethylformamide.

Another RPM that can be used is $[Co(biphenyldicarboxylate)(4,4'$-bipyridine$)].0.5DMF$. Information can be found in RPM-2: A recyclable porous material with unusual adsorption capability: self assembly via structural transformations, Long Pan et al., Chem. Commun., 2003, pp. 854-855, which incorporated herein by reference in its entirety. In this publication, $[Co(biphenyldicarboxylate)(4,4'$-bipyridine$)].0.5DMF$ is referred to as $[Co(bpdc)(bpy)].0.5DMF$.

Another RPM than can be used is $[Zn_2(biphenyldicarboxylate)_2(1,2$-bipyridylethene$)].2DMF$. Information can be found in RPM3: A Multifunctional Microporous MOF with Recyclable Framework and High $H_2$ Binding Energy, Anjian Lan et al., Inorg. Chem. 2009, 48, pp. 7165-7173, which incorporated herein in its entirety, and in A Luminescent Microporous Metal_organic Framework for the Fast and Reversible Detection of High Explosives, Anjian Lan, Angew. Chem. Int. Ed. 2009, 48, pp. 2334-2338, which incorporated herein by reference in its entirety. In this reference, $[Zn_2(biphenyldicarboxylate)_2(1,2$-bipyridylethene$)].2DMF$ is referred to as $[Zn_2(bpdc)_2(bpee)].2DMF$, wherein bpee is 1,2-bipyridylethene.

Another RPM that can be used is $Mg_3(O_2C-C_{10}-H_6-CO_2)_3$. Information on this MOF can be found in Strong H2 Binding and Selective Gas Adsorption within the Microporous Coordination Solid $Mg_3(O_2C-C_{10}-H_6-CO_2)_3$, Mircea Dinca et al., J. Am. Chem. Soc., 2005, 127, pp. 9376-9377, which incorporated herein by reference in its entirety.

The RPMs listed above are solids present in a solvent (such as DMF and water). After the network is formed, the solvent can be driven off by heating.

The RPM containing the material can be incorporated in an anhydrous composition. By anhydrous it is means that the composition contains less than 5% free water. In certain embodiments, there is no free water. When calculating the water, water molecules that are part of a hydrate of a material are not counted.

The anhydrous composition comprises a base. The base can be any conventional composition. In some embodiments, the composition is an antiperspirant and/or deodorant composition. Examples of these types of compositions are sticks, soft solids, gels, and aerosols. The composition can also be a perfume composition. Antiperspirant/deodorants are applied to axillary areas of a person.

The material can be any material whose molecules can adsorb into the pores of the RPM. Examples of materials include, but are not limited to, fragrance, flavoring agent, antioxidants, vitamins, and, coenzyme Q10.

In one embodiment, the material is a fragrance. By delivering fragrance that is adsorbed into the pores of the RPM, fragrance can be delivered to a person and stored until needed. For antiperspirants/deodorants, fragrance will be released as a person perspires and sweat (water) is released and contacted with the RPM. Fragrance will be delivered when it is needed to mask the odors associated with sweating. In certain embodiments, RPMs can hold an amount of fragrance that is up to 80% of the weight of the RPM.

The amount of RPM used depends on the holding capacity of the RPM. Typically, the amount of fragrance in a composition is 0.1 to 5 weight % of the composition. Using an RPM can reduce the amount of fragrance needed for a composition because the fragrance can be released when needed. Typically, excess fragrance is needed in a composition to maintain the fragrance in the composition over the intended use of the product. For antiperspirants/deodorants, this is typically 24 hours.

Fragrance molecules that can be used are any that have a size that fit within the pores of the RPM. Additional fragrance molecules that do not fit within the RPM can be included in the base portion of the composition. Overall, the composition can contain fragrance molecules that all fit within the RPM or a portion fit within the RPM and a portion is in the base. Fragrances can be optimized for each specific RPM based on physical and chemical properties that include solubility, volatility, stability, molecular size, chemical functionality (alcohols, esters, aldehydes, ketones, etc.), cost, odor impact (threshold and intensity), ability to reduce malodor perception through various means, and odor character (to provide range of character for creative perfumery). These fragrances can be synthetic fragrance materials or they can be extracts of natural products, such as essential oils.

In another embodiment, the material can be a flavoring agent. An RPM containing a flavoring agent can be incorporated into any anhydrous composition that contains a flavoring agent. In some embodiments, the composition can be an oral care composition.

Specific Emobiments

Fragrance release was examined in a closed system using NMR (Varian VNMRS 300 MHz over a period of ten hours) at 25° C. Using the free fragrance in deuterium oxide as the backdrop, fragrance in $RPM_3$-Zn was measured hourly to see the increasing intensity of the fragrance. The fragrance used was Ethyl Butyrate, a hydrophobic fragrance.

Each prepared sample had 3.5 mg (3.98 µL) Ethyl Butyrate. For this, fragranced RPM3-Zn was used containing 14% ethyl butyrate. The first sample was the free fragrance and was prepared as follows: 3.98 µL in 500 µL $D_2O$. The second sample was 25 mg of RPM3-Zn (14% fragrance=3.5 mg) in 500 µL $D_2O$.

In the NMR study, a steady increase was observed and then the intensity remained constant once reaching the maximum fragrance abundance. The free fragrance has a linear behavior in that over time, its intensity is constant. The RPM3-Zn on the other hand shows an increasing trend where once maximum abundance is reached, a steady linear behavior occurs. The table below lists the data.

| Time | 24.998 mg RPM3-Zn + 500 µL $D_2O$ Fragrance Intensity | Free Fragrance Intensity 4 µL Ethyl Butyrate + 500 µL $D_2O$ |
|---|---|---|
| Instantaneous | 117641 | 4422402 |
| One hour | 1250242 | |
| Two hours | 2750685 | |
| Three hours | 2934370 | 4676620 |
| Four hours | 2859726 | |
| Five Hours | 3029066 | |
| Six Hours | 3199534 | 4650881 |
| Seven Hours | 3393394 | |
| Eight Hours | 3494312 | |
| Nine hours | 3149451 | 4640791 |
| Ten Hours | 3639734 | |

The above testing was repeated except that the fragrance used was D-limonene, which is a hydrophilic fragrance, and the system was open. The same weight loading of fragrance was used.

| Time | 24.998 mg RPM3-Zn + 500 µL $D_2O$ Fragrance Intensity | Free Fragrance Intensity 4 µL D-limonene + 500 µL $D_2O$ |
|---|---|---|
| Instantaneous | 0 | 936335 |
| One hour | 0 | 900514 |
| Two hours | 160474 | 835111 |
| Three hours | 287598 | 692984 |
| Four hours | 491047 | 400856 |
| Five Hours | 236325 | 145169 |
| Six Hours | 222454 | 96834 |
| Seven Hours | 233437 | 0 |
| Eight Hours | 238739 | 0 |
| Nine hours | 236447 | 0 |
| Ten Hours | 234271 | 0 |

The free fragrance had a linear decrease in intensity, and it completely left the solvent after seven hours. The RPM3-Zn had a ramp up in intensity through the first couple of hours, and then it had a steady release of fragrance.

What is claimed is:

1. A method of delivering a material to a person comprising directly applying an anhydrous antiperspirant and/or deodorant composition to an axillary area of a person, wherein
   a) the anhydrous composition comprises a base and metal organic framework formed from a recyclable porous material (RPM) with the material adsorbed into the metal organic framework, and b) the recyclable porous material has a structure that breaks down when contacted with water to release the material.

2. The method of claim 1, wherein the anhydrous composition is a stick, an aerosol, a soft solid, or a gel.

3. The method of claim 1, wherein the metal organic framework is formed from an RPM selected from the group consisting of [$Co_3$(biphenyldicarboxylate)$_3$4,4'-bipyridine], [Co(biphenyldicarboxylate)(4,4'-bipyridine)], [$Zn_2$(biphenyldicarboxylate)$_2$(1,2-bipyridylethene)], $Mg_3$($O_2C$—$C_{10}$—$H_6$—$CO_2$)$_3$, and combinations thereof.

4. The method of claim 3, wherein the RPM is [$Co_3$(biphenyldicarboxylate)$_3$4,4'-bipyridine].

5. The method of claim 3, wherein the RPM is [Co(biphenyldicarboxylate)(4,4'-bipyridine)].

6. The method of claim 3, wherein the MOF is [$Zn_2$(biphenyldicarboxylate)$_2$(1,2-bipyridylethene)].

7. The method of claim 3, wherein the RPM is $Mg_3$($O_2C$—$C_{10}$—$H_6$—$CO_2$)$_3$.

8. The method of claim 1, wherein the material is at least one material chosen from fragrance, flavoring agent, antioxidant, vitamin, and coenzyme Q10.

9. The method of claim 1, wherein the material comprises a fragrance.

* * * * *